(12) United States Patent
Konawa (10) Patent No.: US 8,486,037 B2
(45) Date of Patent: Jul. 16, 2013

(54) ABSORBENT ARTICLE HAVING RELEASABLE FLAP COVERS

(75) Inventor: Satoko Konawa, Sakura (JP)

(73) Assignee: Daio Paper Corporation, Ehime (JP)

(*) Notice: Subject to any disclaimer, the term of this patent is extended or adjusted under 35 U.S.C. 154(b) by 571 days.

(21) Appl. No.: 12/680,304

(22) PCT Filed: Sep. 25, 2008

(86) PCT No.: PCT/JP2008/067321
§ 371 (c)(1),
(2), (4) Date: Mar. 26, 2010

(87) PCT Pub. No.: WO2009/041517
PCT Pub. Date: Apr. 2, 2009

(65) Prior Publication Data
US 2010/0256585 A1    Oct. 7, 2010

(30) Foreign Application Priority Data
Sep. 26, 2007    (JP) .................... 2007-248348

(51) Int. Cl.
*A61F 13/15*    (2006.01)
*A61F 13/20*    (2006.01)

(52) U.S. Cl.
USPC ................. 604/385.05; 604/385.04

(58) Field of Classification Search
USPC ............ 604/385.01, 385.03, 385.04, 385.05
See application file for complete search history.

(56) References Cited

U.S. PATENT DOCUMENTS

| | | | | |
|---|---|---|---|---|
| 5,330,461 A | * | 7/1994 | Leeker | 604/385.04 |
| 6,168,582 B1 | * | 1/2001 | Hasegawa | 604/385.02 |
| 2007/0197991 A1 | * | 8/2007 | Wetter et al. | 604/385.05 |

FOREIGN PATENT DOCUMENTS

| | | |
|---|---|---|
| JP | 4-103117 | 9/1992 |
| JP | 8-066427 | 3/1996 |
| JP | 9-094267 | 4/1997 |
| JP | 2007-054601 | 3/2007 |
| JP | 2007-075137 | 3/2007 |

* cited by examiner

*Primary Examiner* — Lynne Anderson
*Assistant Examiner* — Aundria Hairell
(74) *Attorney, Agent, or Firm* — Jordan and Hamburg LLP (57) ABSTRACT

An absorbent article which can be fixed to an undergarment without creating wrinkles, a release paper sheet is composed of a first release paper sheet covering a main body displacement-preventing adhesive layer and wing displacement-preventing adhesive layers and a pair of second release paper sheets respectively covering seat displacement-preventing adhesive layers. When the article is applied to shorts, the first release paper sheet is removed, and the main body displacement-preventing adhesive layer and the wing displacement-preventing adhesive layers of the absorbent article are fixed to the shorts that are pulled down. Then, the shorts are pulled up and worn, and the second release paper sheets are removed to fix the seat displacement-preventing adhesive layers to the shorts.

4 Claims, 8 Drawing Sheets

ABSORBENT ARTICLE HAVING RELEASABLE FLAP COVERS

BACKGROUND OF THE INVENTION

The present invention relates to an absorbent article such as a sanitary napkin, a pantiliner, or an incontinence pad for absorbing menstrual blood, vaginal discharge, or the like, and, specifically, relates to an absorbent article in which adhesive layers are provided to wing-like flaps, which are used so as to wrap around the crotch portion of an undergarment for fixing the absorbent article to the undergarment, and provided to seat-holding flaps to be positioned at the seat position of the undergarment posteriorly of the wing-like flaps.

Conventionally known absorbent articles such as sanitary napkins, pantiliners, vaginal discharge sheets, and incontinence pads are those each having an absorber composed of cotton-like pulp or the like interposed between a liquid-impermeable back sheet composed of a polyethylene sheet, a polyethylene laminated nonwoven fabric, or the like and a liquid-permeable front sheet composed of a nonwoven fabric, a porous plastic sheet, or the like.

In some of such absorbent articles, in order to prevent displacement when it is being worn, for example, one or more lines of adhesive layers are provided to the absorber on the skin-non-contact side (the outer surface of the liquid-impermeable back sheet), and wing-like flaps provided in a unified manner extend outward from both side edges relative to the longitudinal direction of the napkin body and are provided with adhesive layers on the skin-non-contact side. Furthermore, a pair of integral seat-holding flaps posteriorly of the wing-like flaps so as to be positioned outward from the absorber is provided with adhesive layers on the skin-non-contact side. In addition, the absorbent article individually packaged is provided with a single release paper sheet for covering all the adhesive layers.

When the absorbent article is fixed to an undergarment, the release paper sheet covering all the adhesive layers is thoroughly removed, then the absorbent article is fixed to an appropriate position of the undergarment that is pulled down, and the wing-like flaps protruding sideward are folded at the returning lines so as to wrap around the crotch portion of the undergarment and thereby to adhere to the outer surface of the crotch portion of the undergarment.

However, when the absorbent article is attached to the undergarment after the release paper sheet is thoroughly removed, since the absorber is not interposed in the wing-like flaps and the seat-holding flaps, the flaps are readily turned or bended during the attaching work. As a result, the adhesive layers provided to the flap portions adhere to the adhesive layers provided to the main body, which causes a problem that the flap portions will be broken by forcibly removing the adhesive layers from each other.

Accordingly, as described in JP-A-2007-54601 and JP-A-2007-75137, a structure for partially removing a release paper sheet when an absorbent article is fixed to an undergarment is recently employed.

That is, JP-A-2007-54601 discloses a sanitary napkin having a main body adhesive layer; a pair of wing portions and a pair of posterior flap portions that are folded to the skin-contact side of the main body at both sides relative to the longitudinal direction of the main body; a wing portion adhesive portion on the surface of each wing portion on the back sheet side for fixing the sanitary napkin to the skin-non-facing surface of clothing such as shorts; and a posterior flap portion adhesive portion on the surface of each posterior flap portion on the back sheet side for fixing the sanitary napkin to the clothing such as shorts on the skin-facing side. The sanitary napkin has a wrapping structure in which a second sheet portion covers a part of the main body adhesive layer and is folded from the posterior end of the napkin to the skin-contact side, and the protruding portion covers the wing portion adhesive portion and the posterior flap portion adhesive portion. In the wrapping structure, the napkin is set on the clothing such as shorts on the skin-facing side, maintaining the state that the wing portion adhesive portion and the posterior flap portion adhesive portion are covered with the protruding portion of the second sheet portion, and then the protruding portion is removed from both the adhesive portions, and the protruding portion of the second sheet portion is further pulled to remove it from the main body adhesive layer.

JP-A-2007-75137 discloses a packaged sanitary napkin having an anterior adhesive layer and a wing portion adhesive layer in a front half of the main body, approximately; an anterior protection sheet having a size capable of covering the adhesive layers; two lines of posterior adhesive areas, apart from each other in the width direction, near the central line in the longitudinal direction of the main body in a back half of the main body, approximately; two pairs of auxiliary posterior adhesive areas, apart from each other in the longitudinal direction, on both sides of the posterior adhesive areas; and a posterior protection sheet having a size capable of covering these adhesive layers. The sanitary napkin is set on shorts bring worn, in the state that only the anterior protection sheet is removed, and then the posterior portion is attached to the shorts by pulling the posterior protection sheet backward.

SUMMARY OF INVENTION

However, in the wrapping structure of the absorbent article described in JP-A-2007-54601, after a part of the main body adhesive layer is temporarily attached to an undergarment, then the second sheet portion covering the wing portion adhesive portion and so on is removed. Therefore, when it is recognized that the wing portion is not placed at an appropriate position after the second sheet portion is removed, the napkin must be re-fixed. On this occasion, the adhesive portions of the wing portion and the posterior flap portion may adhere to improper positions. In addition, since the napkin is fixed to an undergarment that is pulled down, after the fixation of the napkin, the undergarment is extended when it is pulled up, but the extension of the undergarment is restricted at the portion adhering to the napkin, in particular, at the buttock (i.e., seat) portion. This causes problems that wrinkles and twists are made in the undergarment to cause an uncomfortable feeling or that the fixation of the napkin to the undergarment deviates from an appropriate position.

In addition, in the packaging of the sanitary napkin described in JP-A-2007-75137, since the napkin is attached to an undergarment in the state that the anterior protection sheet covering the wing portion adhesive layer and so on is removed, the wing portion is fixed to an appropriate position at one time. However, when the undergarment is pulled up after the fixation of the napkin to the undergarment, the above-mentioned problems of wrinkles of the undergarment and detachment from the undergarment may occur.

Accordingly, the main object of the preset invention is to provide an absorbent article that can be smoothly set to an undergarment and be fixed to the undergarment at an appropriate position and also can be fixed to the undergarment without causing wrinkling.

In order to solve the above-mentioned problems, in a first aspect of the present invention provided is an absorbent article including wing-like flaps that are respectively disposed on both side edges of a main body in which an absorber is interposed between a liquid-permeable front sheet and a back sheet and that are fixed to an undergarment by wrapping around a crotch portion of the undergarment when the article is worn; seat-holding flaps that are respectively disposed on both side edges of the main body posteriorly of the wing-like flaps and that are fixed on the inner side of the undergarment at the buttock (i.e., seat) portion when the article is worn; a main body displacement-preventing adhesive layer on the back side of the absorber; wing displacement-preventing adhesive layers on the back sides of the wing-like flaps; seat displacement-preventing adhesive layers on the back sides of the seat-holding flaps; and removable release paper sheets covering the main body displacement-preventing adhesive layer, the wing displacement-preventing adhesive layers, and the seat displacement-preventing adhesive layers, wherein the release paper sheets are constituted of a first release paper sheet covering the main body displacement-preventing adhesive layer and the wing displacement-preventing adhesive layers and a pair of second release paper sheets respectively covering the seat displacement-preventing adhesive layers.

In the first aspect of the invention, the release paper is constituted of the first release paper sheet covering the main body displacement-preventing adhesive layer and the wing displacement-preventing adhesive layers and the pair of second release paper sheets respectively covering the seat displacement-preventing adhesive layers.

When the absorbent article is set into shorts, first, the first release paper sheet is removed so that the main body displacement-preventing adhesive layer and the wing displacement-preventing adhesive layers are exposed, and then the absorbent article is fixed to the shorts that are pulled down. Then, the shorts are pulled up and worn, and the second release paper sheets are removed for fixing the seat displacement-preventing adhesive layers to the shorts in the pulled-up state.

Therefore, the absorbent article can be smoothly set into the undergarment and can be fixed to the undergarment at an appropriate position. Furthermore, since, subsequently, the second release paper sheets are removed for fixing the seat displacement-preventing adhesive layers to the shorts in the state that the shorts are pulled up and worn, the seat displacement-preventing adhesive layers are prevented from being wrongly attached to other portions. In addition, since the undergarment is extended along the shape of the body when the seat displacement-preventing adhesive layers are fixed, the layers can be fixed without causing wrinkles in the undergarment.

As a second aspect of the invention, provided is the absorbent article according to the first aspect, wherein the seat-holding flaps, together with the second release paper sheets, are folded to the back side of the absorbent article; the ends of the seat-holding flaps, together with the second release paper sheets, are further folded outward in a Z shape so that the ends of the second release paper sheets protrude from the side edges of the seat-holding flaps.

The second aspect of the invention defines a first embodiment of the absorbent article suitable for being fixed to an undergarment (such as "shorts") by a method as hereinabove described, and since the seat-holding flaps are folded in a Z shape so that the ends of the second release paper sheets protrude from the side edges of the seat-holding flaps, the absorbent article can be easily expanded by pinching the protruding portions when it is worn. This makes the wearing work easy.

As a third aspect of the invention, provided is the absorbent article according to the first aspect, wherein the seat-holding flaps, together with the second release paper sheets, are folded to the back side of the absorbent article, and the ends of the second release paper sheets protrude from the side edges of the seat-holding flaps.

The third aspect of the invention defines a second embodiment of the absorbent article suitable for being fixed to an undergarment (such as "shorts") by a method as hereinabove described, and protrude from the seat-holding flaps, the absorbent article can be easily expanded by pinching the protruding portion when the absorbent article is worn. This makes the wearing work easy.

According to the fourth aspect of the present invention, in the absorbent article of the third aspect the protruding portions of the second release paper sheets are each provided with a pinching tab folded toward the opposite side for being easily pinched.

As the present invention according to claim 5, provided is the absorbent article of any of the first to fourth aspects, wherein a plurality of mutually spaced lines of the seat displacement-preventing adhesive layers are disposed.

The fifth aspect of the invention defines a third embodiment of the absorbent article suitable for being fixed to an undergarment (such as "shorts") by a method as hereinabove described, and the arrangement of the seat displacement-preventing adhesive layers is improved so that the removal resistance of the second release paper sheets is reduced.

According to the present invention as described above, the absorbent article can be smoothly set into an undergarment and be fixed to the undergarment at an appropriate position, and also the seat displacement-preventing adhesive layers can be correctly expanded without being wrongly attached to other portions. In addition, since the seat-holding flaps are expanded and fixed to shorts that are worn, the fixation can be performed without causing wrinkles in the undergarment.

DETAILED DESCRIPTION OF THE INVENTION

Embodiments of the present invention will be described below in detail with reference to drawings.

[Basic Structure of Sanitary Napkin 1]

Figure 1:
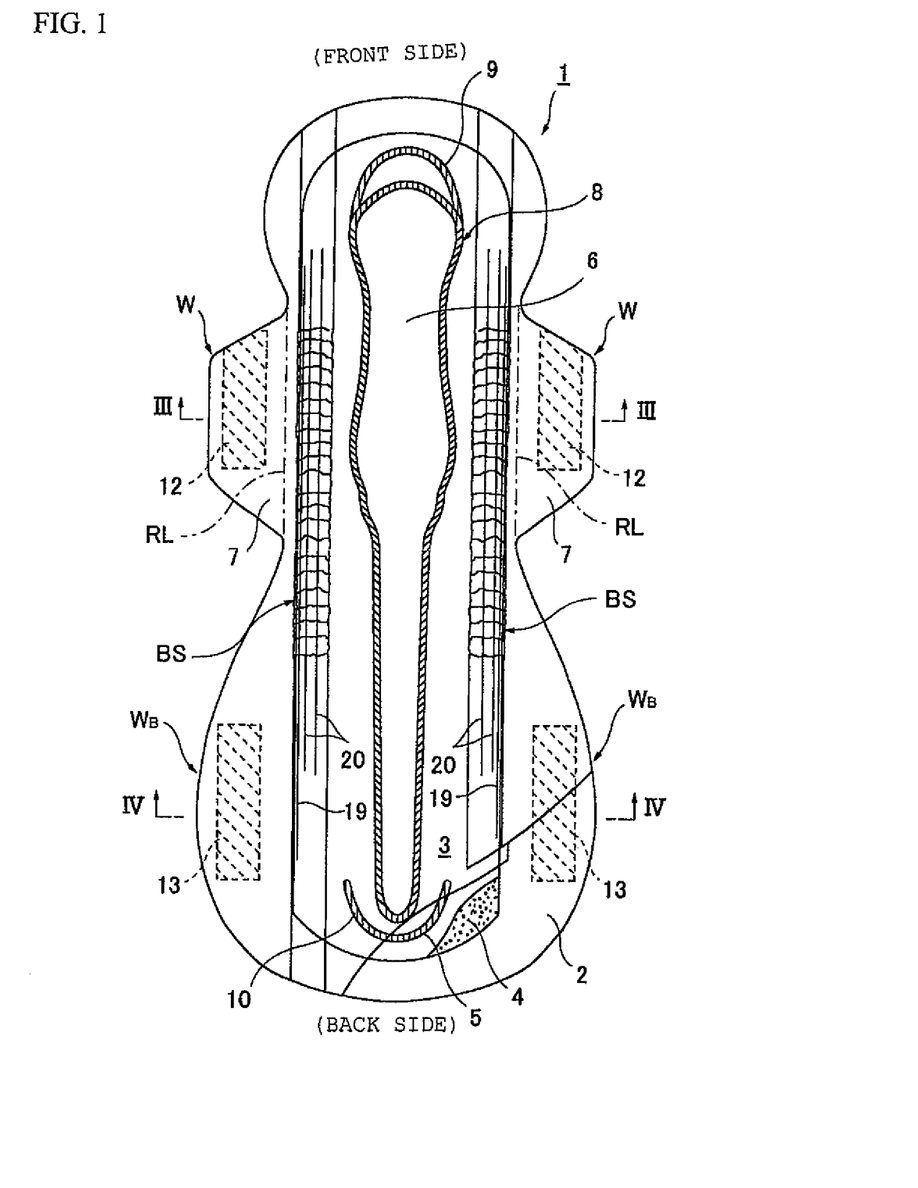
FIG. 1 is a development view of a referential sanitary napkin 1.
Figure 2:
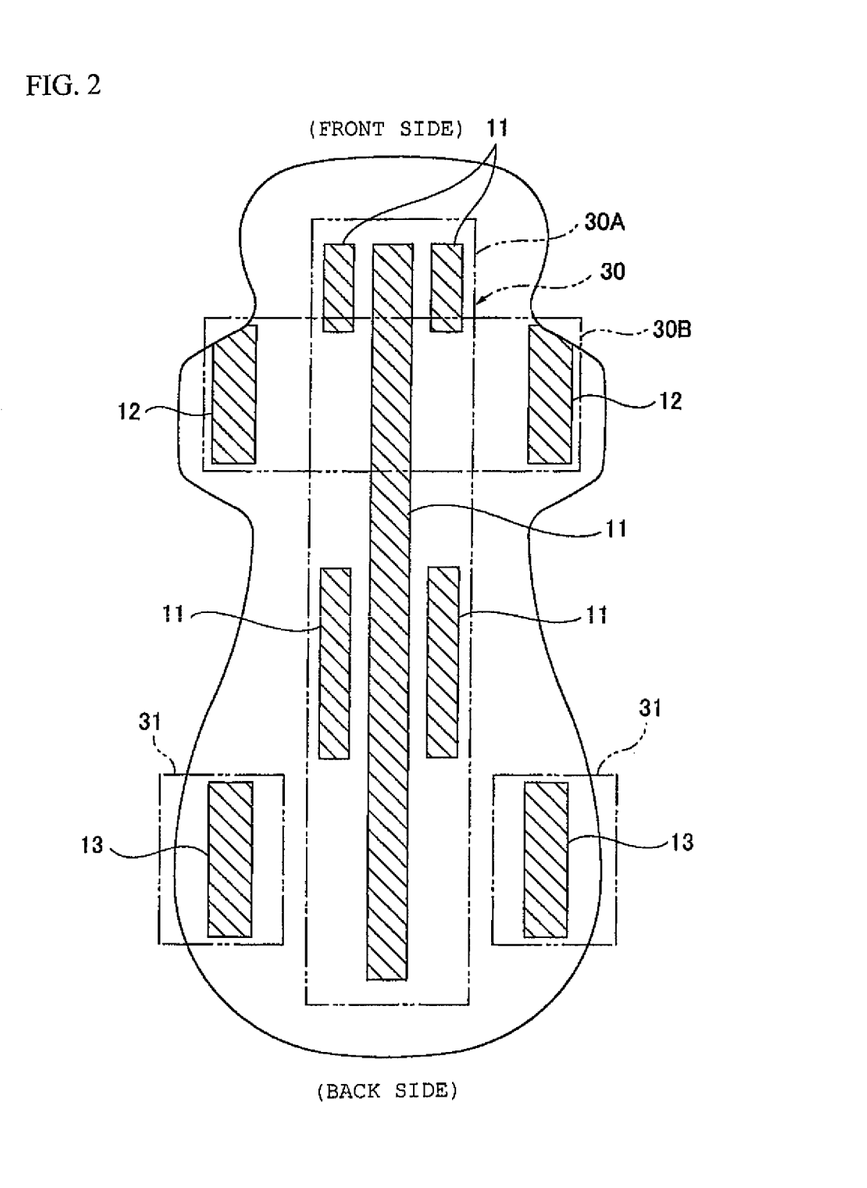
FIG. 2 is a development view of the back side of a sanitary napkin according to the present invention.
Figure 3:
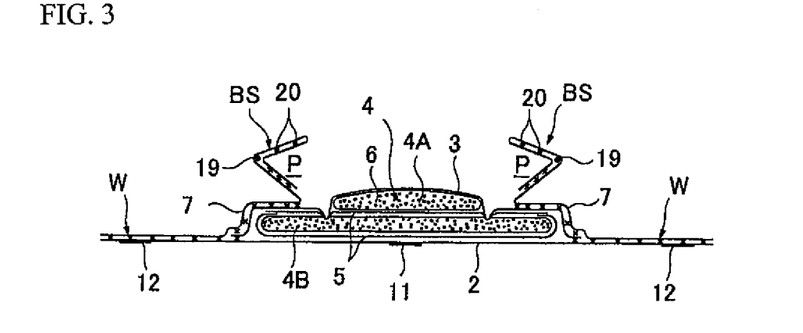
FIG. 3 is a fragmentary view taken along the III-III line in FIG. 1.
Figure 4:
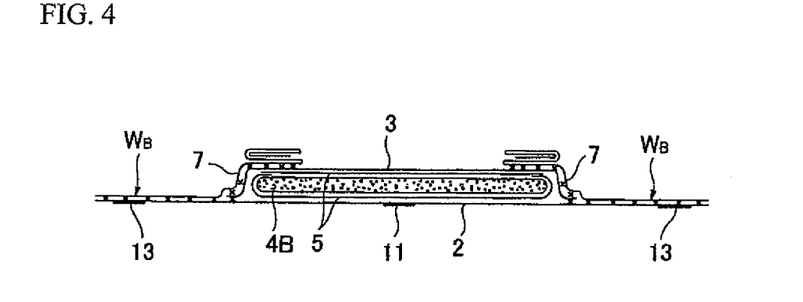
FIG. 4 is a fragmentary view taken along the IV-IV line in FIG. 1.

FIG. 1 is a partially broken sectional development view of a sanitary napkin 1 according to a first embodiment of the present invention, FIG. 2 is a back view thereof, FIG. 3 is a fragmentary view taken along the III-III line in FIG. 1, and FIG. 4 is a fragmentary view taken along the IV-IV line in FIG. 1.

The sanitary napkin 1 is mainly constituted of a liquid-impermeable back sheet 2 composed of a polyethylene sheet or the like; a liquid-permeable top sheet 3 that allows menstrual blood, vaginal discharge, or the like to rapidly permeate; absorbers 4 and 6 composed of cotton-like pulp, synthetic pulp, or the like and interposed between the sheets 2 and 3; creped paper 5 surrounding the absorber 4 for maintaining the shape and increasing the diffusing ability of the absorber 4; and a pair of three-dimensional gathers BS and BS on either side configured so as to have the standing base ends approximately at the side edges of the absorber 4 and to extend toward the front in a predetermined zone in the longitudinal direction so as to include at least body fluid discharge portions. Furthermore, the outer edges of the liquid-impermeable back sheet 2 and the liquid-permeable top sheet 3 are bonded to each other with an adhesive such as hot melt or by adhesion means such as heat sealing at the upper and lower ends in the area surrounding the absorber 4. The side ends of the liquid-impermeable back sheet 2 extending further sideward than the absorber 4 are bonded to the corresponding nonwoven fabrics 7 constituting the three-dimensional gathers BS with an adhesive such as hot melt or by adhesion means such as heat sealing. The laminated sheet portions thus formed by the liquid-impermeable back sheet 2 and the side nonwoven fabrics 7 become wing-like flaps W and W protruding sideward and seat-holding flaps $W_B$ and $W_B$ positioned on a portion corresponding to the wearer's buttocks and, hence, posteriorly of the wing-like flaps.

The structure of the sanitary napkin 1 will be further described in detail below.

The liquid-impermeable back sheet 2 is made of a sheet material having at least a waterproof property, such as polyethylene. Recently, from the viewpoint of preventing a damp or humid feeling, a material having moisture permeability tends to be used. As such a waterproof and moisture-permeable sheet material, a micro-porous sheet that is prepared by melt-kneading an inorganic filler in an olefin-based resin such as polyethylene or polypropylene to form a sheet and then uniaxially or biaxially extending it is preferably used. The liquid-impermeable back sheet 2 on which the absorber 4 is arranged has an outer surface on which, as shown in FIG. 2, one or more lines of main body displacement-preventing adhesive layers 11 are disposed. In addition, on the outer surface of the liquid-impermeable back sheet 2 constituting the wing-like flaps W and W, wing displacement-preventing adhesive layers 12 and 12 are respectively formed. On the outer surface of the liquid-impermeable back sheet 2 constituting the seat-holding flaps $W_B$ and $W_B$, seat displacement-preventing adhesive layers 13 and 13 are respectively formed. Thus, the sanitary napkin 1 is fixed to an undergarment when it is worn. As the liquid-impermeable back sheet 2, a polymer laminated nonwoven fabric in which a plastic film and a nonwoven fabric are laminated may be used.

The liquid-permeable top sheet 3 is preferably made of a porous or nonporous nonwoven fabric or a porous plastic sheet. The fibrous base material constituting the nonwoven fabric may be, as well as a synthetic fiber such as an olefin-based (such as polyethylene or polypropylene), polyester-based, or polyamide-based synthetic fiber, a recycled fiber such as rayon or cupra, or a natural fiber such as cotton, and a nonwoven fabric prepared by an arbitrary processing method such as spunlacing, spunbonding, thermal bonding, melt-blowing, or needle punching can be used. Among these processing methods, spunlacing is excellent in flexibility and drape, and the thermal bonding is excellent in bulk and softness. The liquid-permeable top sheet 3 provided with a large number of pores can rapidly absorb menstrual blood, vaginal discharge, or the like (hereinafter collectively referred to as body fluid), and is therefore excellent in dry feeling.

The absorber 4 has a structure in which an upper layer absorber 4A and a lower layer absorber 4B are stacked. The lower layer absorber 4B has a planar shape defining the outer edge of an absorber region, and the upper layer absorber 4A is arranged for forming a central higher portion 6 of the absorber, having a large height on the use surface side in a region elongated in the longitudinal direction of the napkin in the central portion in the width direction. If the thickness of the central higher portion 6 is too high, the rigidity of the absorber 4 becomes too high, resulting in a reduction in adherence to the body. Therefore, the thickness is 3 to 25 mm and preferably 5 to 18 mm. The upper layer absorber 4A is provided with an embossment 8 proximate the circumferential edge thereof for enclosing thereof and embossments 9 and 10. The embossment 8 is provided for preventing misalignment of the upper layer absorber 4A and also correctly defining the central higher portion 6.

The upper layer absorber 4A contains at least a pulp fiber and a synthetic fiber, and the weight ratio of the pulp fiber and the synthetic fiber is 80 to 20:20 to 80 and preferably 40 to 60:60 to 40.

Examples of the synthetic fiber include polyolefins such as polyethylene and polypropylene, polyesters such as polyethylene terephthalate and polybutylene terephthalate, polyamides such as nylon, and copolymers thereof. A mixture of two or more thereof may be used. In addition, a core-sheath type fiber composed of a fiber having a high melting point as the core and a fiber having a low melting point as the sheath, a side-by-side type fiber, or a composite fiber such as a divided type fiber can be also used. When the synthetic fiber is a hydrophobic fiber, surface treatment with a hydrophilization agent is desirably conducted for obtaining hydrophilicity to body fluid.

The upper layer absorber 4A can contain a highly water-absorbent resin. Examples of the highly absorbent resin include cross-linked polyacrylate, self-cross-linked polyacrylate, saponified products of cross-linked acrylic acid ester/vinyl acetate copolymers, cross-linked isobutylene/maleic acid anhydride copolymers, cross-linked polysulfonate, and partially cross-linked water swellable polymers such as polyethylene oxide and polyacrylic amide. Among them, acrylic acid or acrylate-based resins are excellent in the water absorbing amount and water absorbing rate and are therefore preferred. The water absorbing capacity and the water absorbing rate of the highly water-absorbent resin having a high water absorbing ability can be controlled by adjusting the cross-linking density and the cross-linking density gradient in the manufacturing process. When the blending amount of the resin is large, a so-called gel blocking phenomenon occurs. Since the upper layer absorber 4A is required to accelerate infiltration to the lower layer absorber 4B side, the blending amount is preferably 1 to 10% by weight based on the total weight of the pulp fiber and the synthetic fiber. When the content ratio of the highly water-absorbent resin is higher than 50%, tangling of the pulp fiber is reduced, resulting in a reduction in sheet strength. This readily causes breakage, fracture, and so on and is therefore undesired.

Examples of the pulp fiber include those composed of cellulose fibers such as chemical pulp made from wood and melting pulp, and artificial cellulose fibers such as rayon and acetate. Softwood pulp has a longer fiber length than hardwood pulp and is preferably used in the light of function and cost.

On the other hand, the lower layer absorber 4B does not contain a synthetic fiber and can be made of a pulp fiber alone or a mixture of a pulp fiber and a highly water-absorbent resin. The lower layer absorber 4B is not required to have high permeability, but is desired to hold body fluid infiltrating from the upper layer absorber 4A therein and retain it from oozing to the outside. Therefore, it is preferred not to contain the synthetic fiber. In addition, the content ratio of the highly absorbent resin is desirably 1 to 20% by weight to the total weight of the fiber constituting the lower layer absorber 4B, in order to absorb and hold body fluid.

Incidentally, in the examples shown by the drawings, the liquid-permeable top sheet 3 has a width slightly greater than the width of the absorber 4, as shown by the lateral cross-section views in FIGS. 3 and 4, and merely covers the absorber 4. The three-dimensional gathers BS are constituted of side nonwoven fabrics 7 other than that of the liquid-permeable top sheet 3, specifically, a nonwoven fabric optionally provided with water-repellent treatment or hydrophilic treatment according to the purpose such as prevention of infiltration of menstrual blood, vaginal discharge, or the like or improvement of texture. Such side nonwoven fabrics 7 can be formed by arbitrarily processing a natural fiber, a synthetic fiber, or a recycled fiber as a base material, but are preferably made of a nonwoven fabric provided with breathability by reducing the basis weight, in order to eliminate a stiff feeling and prevent a damp or humid feeling. Specifically, a nonwoven fabric prepared so as to have a basis weight of 15 to 23 $g/m^2$ is desirable, and preferably used is a water repellency-treated nonwoven fabric coated with, for example, a silicone, paraffin, or alkyl chromic chloride-based water repellent, in order to certainly prevent the permeation of body fluid.

Figure 5:
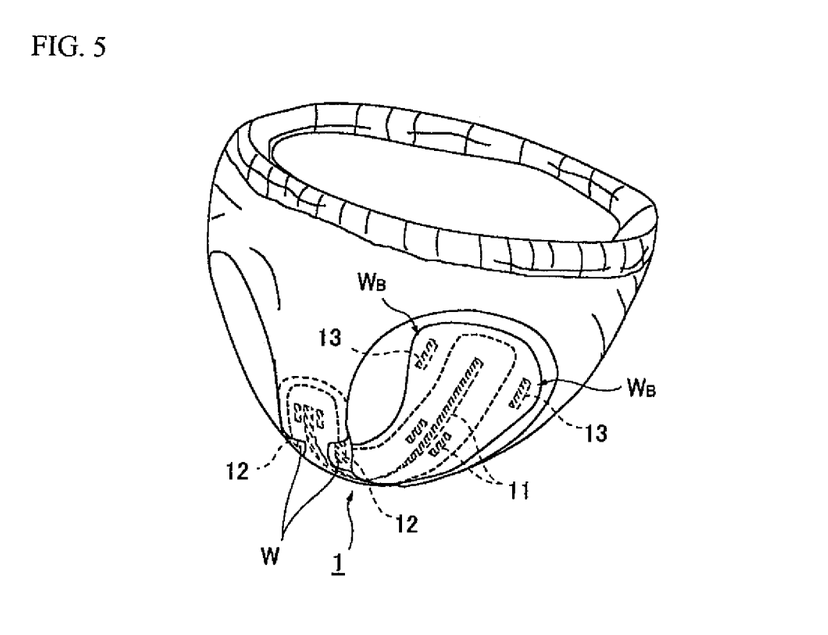
FIG. 5 is a perspective view showing shorts to which a sanitary napkin 1 is attached.

In the side nonwoven fabrics 7, as shown in FIGS. 3 and 4, the outer side portions, exclusive of the middle portion in the width direction, are bonded over an area from the side periphery of the absorber 4, slightly passing beyond the side edges of the absorber, to the outer edges of the liquid-impermeable back sheet 2 with an adhesive such as hot melt, and the laminated sheet portions of the side nonwoven fabrics 7 and the liquid-impermeable back sheet 2 form a pair of the wing-like flaps W and W on either side at the lateral positions of the absorber approximately corresponding to the body fluid discharge portions and form second wing-like flaps $W_B$ and $W_B$ at the positions corresponding to the seat and, hence, posteriorly of the wing-like flaps W and W. The wing-like flaps W and W and the second wing-like flaps $W_B$ and $W_B$ include adhesive layers 12 and 13 on the outer sides. When the napkin is attached to shorts, as shown in FIG. 5, the wing-like flaps W and W are folded to the opposite side at or near the folding lines RL and are fixed by wrapping around the crotch portion of the shorts.

Furthermore, the inside portion of each side nonwoven fabric 7 is approximately doubly folded, and a stringlike elastic stretchable member 19 is arranged in the middle portion in the height direction inside the double sheet and is fixed at both ends or an appropriate position thereof in the longitudinal direction. In addition, a plurality, two in the example shown in the drawings, of stringlike elastic stretchable members 20 and 20 are arranged at the upper side of the stringlike elastic stretchable member 19 in the state that they are fixed to the sheet at both ends, or an appropriate position thereof in the longitudinal direction. As shown in FIG. 4, the double sheet portion is bonded to the absorber 4 in a state of being folded into a Z-shaped cross-section at the front and back ends. By doing so, the three-dimensional gathers BS and BS that stand on the front side are formed, while forming pockets P and P having openings facing the inside by using the portions arranging the stringlike elastic stretchable members 19 as folding points for forming dogleg-shaped cross-sections.

Furthermore, in the present invention, as shown in FIG. 2, the above-described sanitary napkin 1 is provided with removable release paper sheets covering the adhesive layers 11, 12, and 13 disposed on the outer surface, and is arbitrarily provided with a package sheet (not shown) for covering the further outer surface side into an individually packaged state.

The release paper sheet is constituted of a first release paper sheet 30 covering the main body displacement-preventing adhesive layer 11 and the wing displacement-preventing adhesive layers 12 and a pair of second release paper sheets 31 and 31 respectively covering the seat displacement-preventing adhesive layers 13. As show in FIG. 2, the first release paper sheet 30 is composed of a main body displacement-preventing adhesive layer release paper 30A for covering the main body displacement-preventing adhesive layer 11 arranged long in the central portion in the longitudinal direction of the napkin and a wing displacement-preventing adhesive layer release paper sheet 30B for covering the wing displacement-preventing adhesive layers 12 and 12 arranged in the respective wing-like flaps W and W that are spaced from each other in the width direction, and the release paper 30A and the release paper 30B are bonded to each other at the overlapping part into one piece having an approximate cross shape. The second release paper sheets 31 individually cover the seat displacement-preventing adhesive layers 13, independent from the first release paper sheet 30, and the outer side ends thereof protrude from the side edges of the sanitary napkin 1 (side edges of the seat-holding flaps $W_B$). Furthermore, the first release paper sheet 30 may be formed of one sheet of release paper covering the main body displacement-preventing adhesive layer 11 and the wing displacement-preventing adhesive layers 12.

The release paper sheets 30 and 31 have a function of protecting the adhesive of the adhesive layers 11, 12, and 13. The adhesive layers 11, 12, and 13 are exposed by removing the release paper sheets 30 and 31 when the napkin 1 is worn and are attached to shorts for being fixed. As the release paper sheets 30 and 31, those in which a release agent is applied to a release paper base material are preferably used. As the release paper base material, a film of, for example, polypropylene, low-density polyethylene, or polyvinyl alcohol, a nonwoven fabric, paper, or a composite material thereof can be used. In particular, in the present invention, as described below, since the second release paper sheets 31 are removed after the shorts are pulled up and worn, it is preferable that at least the second release paper sheets 31 be made of a soft material that does not irritate the skin in contact therewith, and a film material is preferred rather than paper. In addition, the release agent is preferably a silicone, fluorine, or isocyanate-based one. In particular, it is preferable to use a silicone resin-based release agent, for example, by being applied to a release paper base material, followed by heating for drying, or by being sprayed to form a thin coating.

Furthermore, the release paper sheets 30 and 31 are preferably subjected to antistatic treatment for preventing static cling to the hand after being removed from the adhesive layers 11 to 13. As a method other than the antistatic treatment, the static cling to the hand can be prevented, for example, by providing adhesive portions to the release paper sheets 30 and 31 so that the adhesive portions of the release paper sheets removed from the adhesive layers can adhere to a package sheet or the like.

Furthermore, if the release paper sheets 30 and 31 are made of a water decomposable material that can be flushed in toilets after the removal, disposal is simple.

However, in the manufacturing process of the sanitary napkin according to the present invention, since the second release paper sheets 31 are disposed independently from the first release paper sheet 30, the folded state of the seat-holding flaps WB may be released by flapping in the conveying process, or the folded position may be varied. Therefore, the seat-holding flaps WB folded toward the outer surface are preferably temporarily fixed for maintaining the folded state by hot-melt adhesion such as heat sealing or ultrasonic sealing that allows easy peeling.

[Method for Wearing Sanitary Napkin]

Now, a method for wearing the sanitary napkin will be described in detail.

Figure 6:
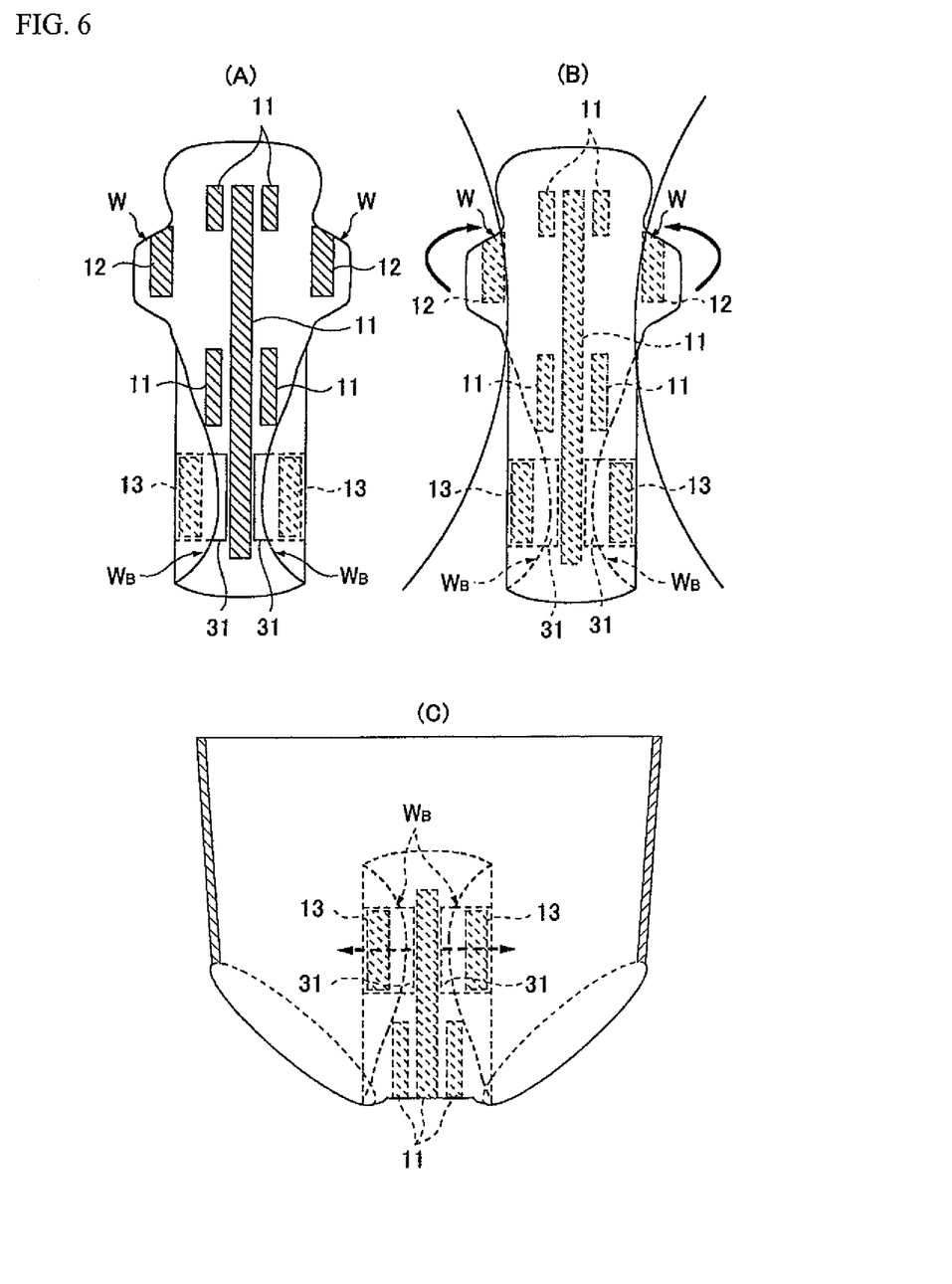
FIG. 6 includes drawings (A) to (C) showing a procedure for attaching the sanitary napkin 1.

As shown in FIG. 6(A), the first release paper sheet 30 is removed from the sanitary napkin, and also the wing-like flaps W and W are spread. On this occasion, the second release paper sheets 31 are still covering the seat displacement-preventing adhesive layers 13, because they are arranged independently from the first release paper sheet 30.

Then, as shown in FIG. 6(B), the wing-like flaps W of the sanitary napkin from which the first release paper sheet 30 has been removed are set into the crotch portion of shorts that are pulled down, and the main body displacement-preventing adhesive layer 11 and the wing displacement-preventing adhesive layers 12 are fixed to the shorts. Thus, the sanitary napkin can be worn while adjusting the positions of the wing-like flaps W to the crotch portion of the shorts and thereby can be correctly positioned in a single operation. In addition, during this fixing work, since the seat displacement-preventing adhesive layers 13 are still covered with the second release paper sheets 31, the seat displacement-preventing adhesive layers 13 can be prevented from adhering to other adhesive layers 11 and 12 and from being bent to adhere to each other.

Then, as shown in FIG. 6(C), in the state that the shorts are pulled up and worn, the seat-holding flaps $W_B$ and $W_B$ are expanded with both hands inserted into the shorts from the back side while removing the second release paper sheets 31 to fix the seat displacement-preventing adhesive layers 13 and 13 to the back side of the shorts. Since the seat displacement-preventing adhesive layers 13 are thus fixed to the shorts that are pulled up and worn, the sanitary napkin can be fixed to the shorts in the state in which the shorts are fit to the body and are extended, wrinkles and twists do not occur in the shorts, and the sanitary napkin 1 can readily fit to the body.

[Embodiment of Second Release Paper Sheet 31]

Next, an embodiment of the sanitary napkin 1 suitable for such a method of wearing described above will be described in detail. In the present invention, as described in detail in the above description of the wearing method, since the second release paper sheets 31 are removed while expanding the seat-holding flaps $W_B$ and $W_B$ to both sides with both hands inserted into the shorts from the back side in the state that the shorts are pulled up and worn, it is preferable that the second release paper sheets 31 have a structure to be easily drawn away. Accordingly, in the present invention, the following configuration is preferably employed.

Figure 7:
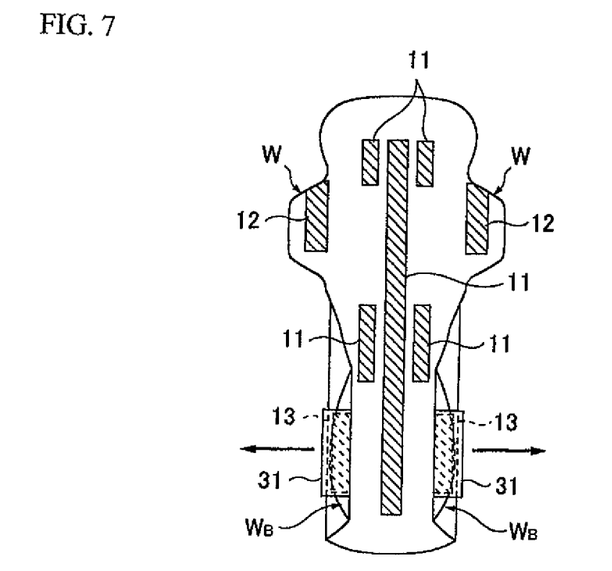
FIG. 7 is a diagram of the back side of a sanitary napkin showing a first embodiment (No. 1).
Figure 8:
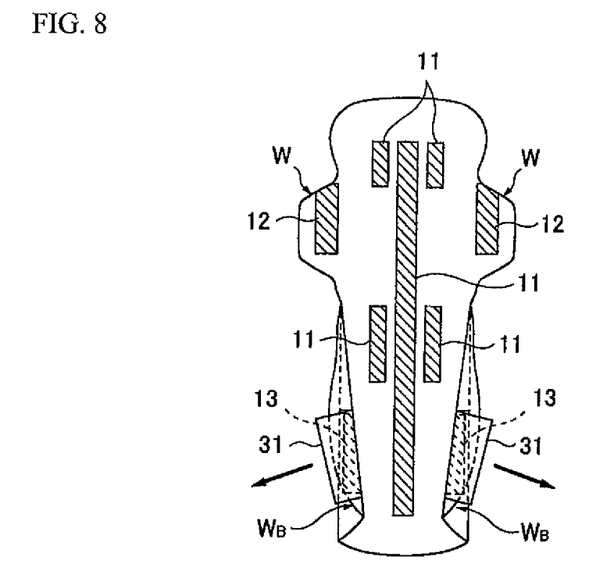
FIG. 8 is a diagram of the back side of the sanitary napkin showing the first embodiment (No. 2).

As shown in FIGS. 7 and 8, in a first embodiment, the seat-holding flaps $W_B$ are folded in a Z shape, and the ends of the second release paper sheets 31 protrude from the side edges of the seat-holding flaps $W_B$. Specifically, as shown in FIG. 7, the seat-holding flaps $W_B$ are, together with the corresponding second release paper sheets 31, folded to the back side of the sanitary napkin 1, and the ends thereof are, together with the corresponding second release paper sheets 31, further folded toward the outer side into a Z shape so that the ends of the second release paper sheets 31 protrude from the side edges of the seat-holding flaps $W_B$.

Furthermore, in the embodiment shown in FIG. 8, the ends of the seat-holding flaps $W_B$ are, together with the corresponding second release paper sheets 31, folded obliquely outward when the seat-holding flaps $W_B$ are folded in a Z shape. On this occasion, the second release paper sheets 31 at the portions folded back are also arranged to be oblique toward the back side of the sanitary napkin 1. By doing so, when the second release paper sheets 31 are expanded with both hands inserted into the shorts from the back side, though the release paper sheets 31 in the embodiment shown in FIG. 7 must be pulled in the approximately horizontal direction, the release paper sheets 31 can be pulled obliquely upward in the embodiment shown in FIG. 8, which makes the operation easy.

Figure 9:
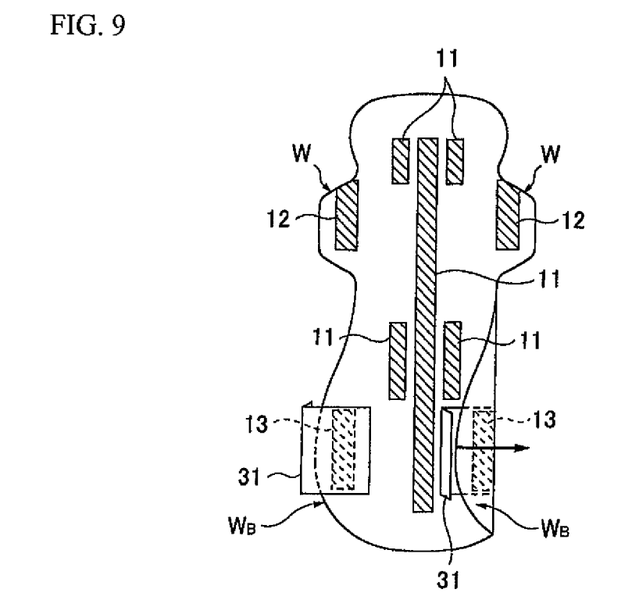
FIG. 9 is a diagram of the back side of a sanitary napkin showing a second embodiment (No. 1).
Figure 10:
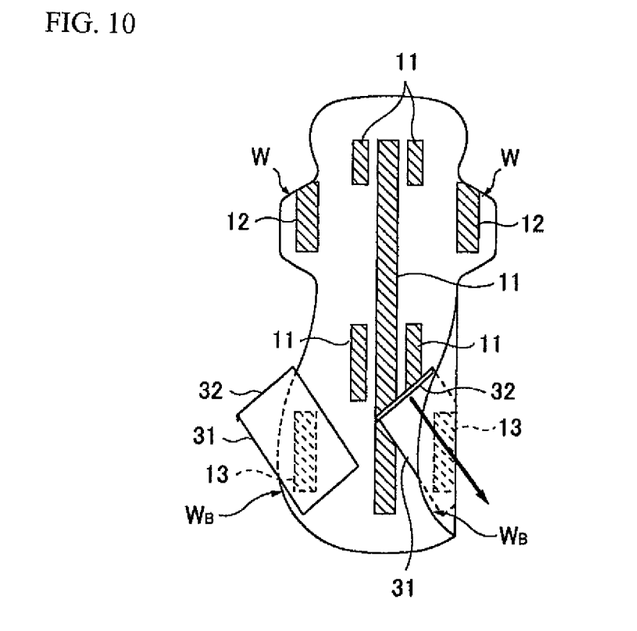
FIG. 10 is a diagram of the back side of the sanitary napkin showing the second embodiment (No. 2).
Figure 11:
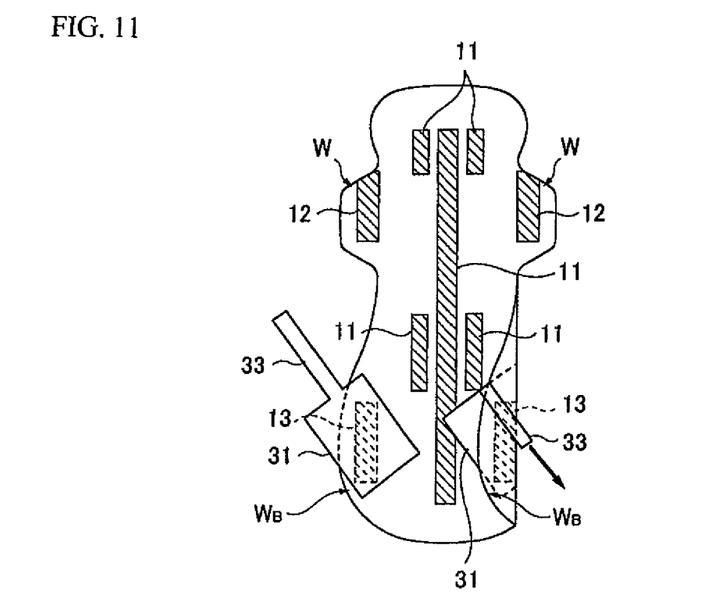
FIG. 11 is a diagram of the back side of the sanitary napkin showing the second embodiment (No. 3).

A second embodiment is one in which, as shown in FIGS. 9 to 11, the ends of the second release paper sheets 31 protrude from the side edges of the seat-holding flaps $W_B$, and the ends are provided with pinching tabs 32 that are folded to the opposite sides.

Specifically, in the example shown in FIG. 9, the seat-holding flaps $W_B$ are folded, together with the second release paper sheets 31, to the back side of the sanitary napkin 1. The second release paper sheets 31 protrude from the side edges of the seat-holding flaps $W_B$, and the ends of the protruding portions are folded to the opposite sides to form pinching tabs 32.

In addition, in the example shown in FIG. 10, the second release paper sheets 31 are disposed so as to be oblique with respect to the width direction of the sanitary napkin 1 and are thereby easily pulled upward. By doing so, the pinching tabs 32 can be pulled obliquely upward when the shorts with the absorbent article are worn. This makes the wearing operation easy.

Furthermore, in the example shown in FIG. 11, instead of pinching tabs 32 in which the ends of the second release paper sheets 31 are folded, a vertically long strip-like pinching tab 33 is provided to the central portion of the end of each of the second release paper sheets 31, and the end of the pinching tab 33 protrudes from the side edge of the seat-holding flap $W_B$ and is folded to the opposite side. By doing so, the tabs can be further easily pinched to make the wearing operation easy.

Figure 12:
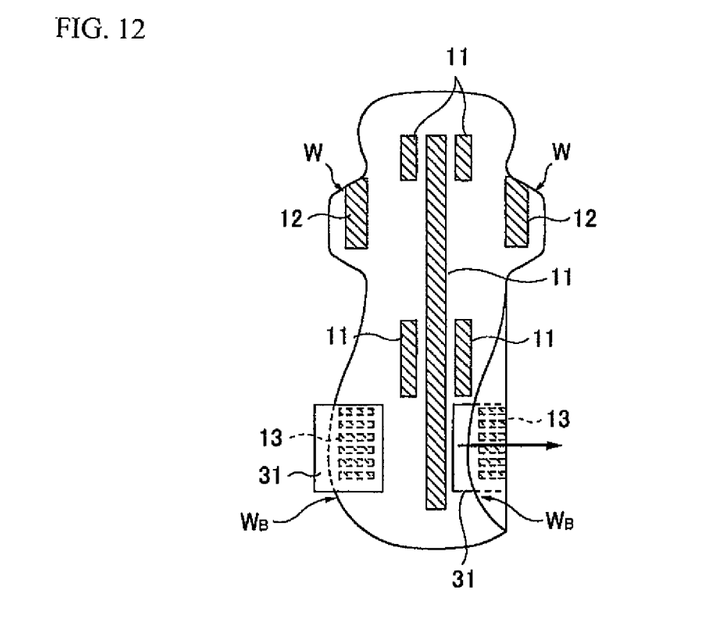
FIG. 12 is a diagram of the back side of a sanitary napkin showing a third embodiment (No. 1).
Figure 13:
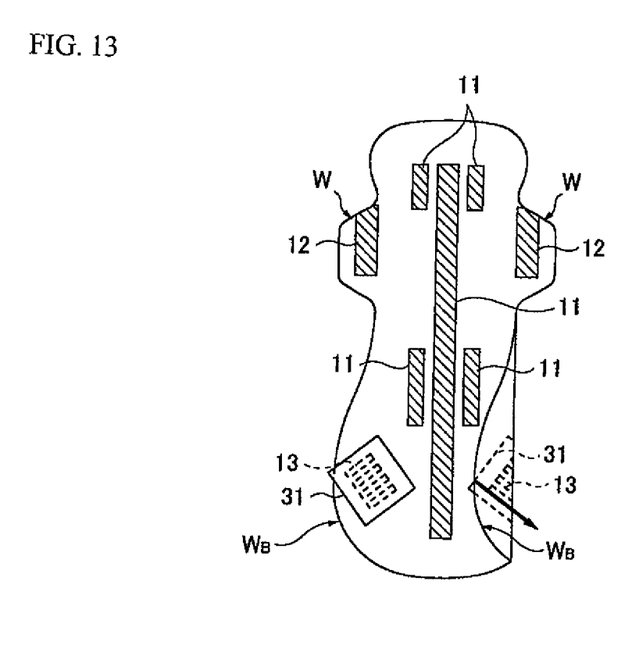
FIG. 13 is a diagram of the back side of the sanitary napkin showing the third embodiment (No. 2).

In a third embodiment, as shown in FIGS. 12 and 13, the arrangement of the seat displacement-preventing adhesive layers 13 is improved. Specifically, in this embodiment, the seat displacement-preventing adhesive layers 13 are composed of a plurality of lines spaced from one another. By doing so, the resistance when the second release paper sheets 31 are removed is reduced to make the wearing operation easy. As shown in FIG. 12, the seat displacement-preventing adhesive layers 13 in such a configuration are arranged along the width direction with spaces therebetween in the longitudinal direction of the sanitary napkin 1, but, as shown in FIG. 13, the seat displacement-preventing adhesive layers 13 may be disposed to be oblique outward. Furthermore, when the seat displacement-preventing adhesive layers 13 are disposed to be oblique, as shown in FIG. 13, the pulling direction of the second release paper sheets 31 when the shorts with the absorbent article are being worn can be controlled as described above by arranging the second release paper sheets 31 along the oblique direction, and thereby the wearing operation can be made easy.

The invention claimed is:

1. An absorbent article comprising:
   wing-like flaps that are respectively disposed on both side edges of a main body in which an absorber is interposed between a liquid-permeable front sheet and a back sheet and are to be fixed to an undergarment by wrapping around an inner surface of a crotch portion of the undergarment when the article is worn;
   seat-holding flaps that are respectively disposed on both side edges of the main body posteriorly of the wing-like flaps and that are to be fixed to an inner surface of a seat portion of the undergarment when the article is worn;
   a main body displacement-preventing adhesive layer on the back sheet adjacent the back side of the absorber;
   wing displacement-preventing adhesive layers on the back sides of the wing-like flaps;
   seat displacement-preventing adhesive layers on the back sides of the seat-holding flaps; and
   removable release paper sheets covering the main body displacement-preventing adhesive layer, the wing displacement-preventing adhesive layers, and the seat displacement-preventing adhesive layers,
      wherein the release paper sheets are constituted of a first release paper sheet covering all the main body displacement-preventing adhesive layer and the wing displacement-preventing adhesive layers so that each of the main body displacement-preventing adhesive layer and the wing displacement-preventing adhesive layer are exposed upon removal of the first release paper sheet in to enable adherence of the main body displacement-preventing adhesive and the wing displacement-preventing adhesive layer to the undergarment in a non-worn state of the undergarment., and a pair of second release paper sheets respectively covering the seat displacement-preventing adhesive layers so that the seat displacement-preventing adhesive layers are exposed separately from the main body displacement-preventing adhesive layer and the wing displacement-preventing adhesive layer upon removal of the second release paper sheets, and
      wherein the seat-holding flaps and the second release paper sheets are each respectively folded to the back side of the absorbent article, and
         the ends of the second release paper sheets protrude from the side edges of the seat-holding flaps, said removal of the second release paper sheets occurring upon the undergarment being positioned in a worn state of the undergarment for enabling the seat displacement-preventing layers to be fitted to a contour of the undergarment at the seat portion thereof.

2. An absorbent article comprising:
   wing-like flaps that are respectively disposed on both side edges of a main body in which an absorber is interposed between a liquid-permeable front sheet and a back sheet and are to be fixed to an undergarment by wrapping around an inner surface of a crotch portion of the undergarment when the article is worn;
   seat-holding flaps that are respectively disposed on both side edges of the main body posteriorly of the wing-like flaps and that are to be fixed to an inner surface of a seat portion of the undergarment when the article is worn;
   a main body displacement-preventing adhesive layer on the back side of the absorber;
   wing displacement-preventing adhesive layers on the back sides of the wing-like flaps;
   seat displacement-preventing adhesive layers on the back sides of the seat-holding flaps; and
   removable release paper sheets covering the main body displacement-preventing adhesive layer, the wing displacement-preventing adhesive layers, and the seat displacement-preventing adhesive layers,
      wherein the release paper sheets are constituted of a first release paper sheet covering all the main body displacement-preventing adhesive layer and the wing displacement-preventing adhesive layers and a pair of second release paper sheets respectively covering the seat displacement-preventing adhesive layers, and
      wherein the seat-holding flaps and the second release paper sheets are each respectively folded to the back side of the absorbent article and
   the ends of the seat-holding flaps and the second release paper sheets are each respectively folded outward in a Z shape so that the ends of the second release paper sheets protrude from the side edges of the hip-holding flaps.

3. The absorbent article according to claim 1, wherein the protruding portions of the second release paper sheets are each provided with a pinching tab folded toward the opposite side.

4. The absorbent article according to any of claims 1 2 or 3, wherein a plurality of mutually spaced lines of the seat displacement-preventing adhesive layers are provided.

* * * * *